United States Patent [19]

Cerefice et al.

[11] 4,005,122
[45] Jan. 25, 1977

[54] POLYHALO POLY CYCLOCARBOXYLIC ACID COMPOUNDS

[75] Inventors: Steven A. Cerefice, Naperville; Ellis K. Fields, River Forest, both of Ill.

[73] Assignee: Standard Oil Company (Indiana), Chicago, Ill.

[22] Filed: Oct. 23, 1975

[21] Appl. No.: 625,191

[52] U.S. Cl. .............................. 260/468 G; 252/8.1; 260/514 G
[51] Int. Cl.² .................. C07C 61/28; C07C 69/74
[58] Field of Search ................. 260/408 G, 514 G

[56] References Cited

OTHER PUBLICATIONS

Engelhard et al., Angew. Chem., Int. Ed. 11, 310 (1972).

*Primary Examiner*—Robert Gerstl
*Attorney, Agent, or Firm*—William H. Magidson; Arthur G. Gilkes; William T. McClain

[57] ABSTRACT

7,7-dihalobicyclo [4.1.0] hept-4-ene-2,3-dicarboxylic acid compounds and 5,5,8,8-tetrahalotricyclo [5.1.0.0$^{4,6}$] octane-2,3-dicarboxylic acid compounds.

6 Claims, No Drawings

POLYHALO POLY CYCLOCARBOXYLIC ACID COMPOUNDS

This invention relates to 7,7-dihalobicyclo [4.1.0] hept-4-ene-2,3-dicarboxylic acid compounds and 5,5,8,8-tetrahalotricyclo [5.1.0.0$^{4,6}$] octane-2,3-dicarboxylic acid compounds.

There has been considerable interest in recent years in new fire-retardant chemicals for use with polymers. Many of these fire-retardants, which are based upon halogenated (brominated and/or chlorinated) compounds, tend to be unstable due to the conjugation of the halogen group or groups with unsaturation in the compounds, such as aromatic unsaturation and/or olefinic unsaturation. Further, many of these compounds are incompatible with the flammable polymeric materials. Accordingly, there is a need for new classes of halogenated compounds suitable for use as fire-retardants in polymeric materials.

The general object of this invention is to provide a new class of halogenated materials. Another object of this invention is to provide a new class of halogenated materials suitable for use as fire-retardants. Other objects appear hereinafter.

We have now found that 7,7-dihalobicyclo [4.1.0] hept-4-ene-2,3-dicarboxylic acid compounds (esters and acids) and 5,5,8,8-tetrahalobicyclo [5.1.0.0$^{4,6}$] octane-2,3-dicarboxylic acid compounds constitute new classes of halogenated compounds suitable for use as fire-retardants. The halogen groups are relatively stable since they are not conjugated with any unsaturation in the molecules. These compounds are very flexible in the sense that the compatibility of the aforesaid compounds can be controlled by suitable choice of hydroxy moiety of the ester. Further, these compounds can be utilized as precursors for the production of biologically active compounds, particularly insecticides.

The compounds of this invention can be represented by the structural formulae:

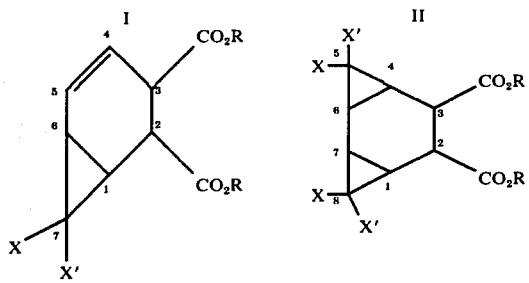

In the above structures each X and X' is halogen, such as bromine or chlorine, and R represents the residue of a monohydroxy compound (monovalent aromatic or aliphatic group whose free valence is bonded to —OH) or hydrogen. For convenience the dihalocarbene compound containing one dihalocarbene group (Structure I) is referred to as a bicyclo compound while those compounds containing two dihalocarbene groups (Structure II) are referred to as tricyclo compounds.

Briefly, the polyhalobicyclo and tricyclocarboxylic acid esters of this invention can be prepared by reacting a suitable 1,2-dihydrophthalic acid compound (acid or ester) with a suitable aryl (trihalomethyl) mercury compound.

The 1,2-dihydrophthalate esters suitable for producing the polyhalobicyclo and tricyclo compounds of this invention incude aliphatic esters containing from 1 to 24 carbon atoms in each aliphatic group such as alkyl esters of 1,2-dihydrophthalic acid containing from 1 to 24 carbon atoms in each alkyl group, such as the dimethyl ester, the diethyl ester, the di-n-propyl ester, the diisopropyl ester, the di-butyl ester, the di-(n-octyl) ester, the di-(2-ethylhexyl) ester, the di-(n-tridecyl) ester, the di-stearyl ester, the ditetracosyl ester, the n-butyl 2-ethylhexyl ester, the di-omega chloro-n-octyl ester, etc.; dialkenyl esters containing from 2 to 24 carbon atoms in each alkenyl group, such as the divinyl esters; the diallyl esters; the dioleyl esters; etc.; the diaromatic esters having from 6 to 24 carbon atoms, such as diaryl esters containing from 6 to 24 carbon atoms, such as diphenyl, di(toluyl), the di-(octadecylphenyl) ester; aralkyl esters containing from 7 to 25 carbon atoms, such as the benzyl ester, chlorobenzyl ester, etc.; mixed esters of two or more of the above types such as the benzyl octyl ester, etc.

The 1,2-dihydrophthalate esters can be produced by reacting the appropriate 1,2-dihydrophthalic acid compound (free acid, acyl halide or anhydride) with a suitable monohydroxy compound at a temperature of 60° to 200° C. or the dimethyl ester can be produced first and the appropriate diester produced by transesterification with a suitable monohydroxy compound at a temperature of 60° to 200° C.

Suitable monohydroxy compounds useful for producing the 1,2-dihydrophthalates include alcohols containing from 1 to 24 carbon atoms such as methyl alcohol, ethyl alcohol, isopropyl alcohol, allyl alcohol, methallyl alcohol, n-butyl alcohol, n-hexyl alcohol, n-octyl alcohol, 2-ethylhexyl alcohol, decyl alcohol, tridecyl alcohol, stearyl alcohol, oleyl alcohol, linoleyl alcohol, linolenyl alcohol, tetracosyl alcohol; aromatic hydroxy compounds containing from 6 to 24 carbon atoms, such as phenol, cresol, para-stearylphenol, naphthol, etc., benzyl alcohol, etc.

These esters can be produced under conventional reaction conditions by reacting from about 1 to 10 moles of monohydroxy compound per carboxyl equivalent of said dihydrophthalic acid compound to form a solution of ester and monohydroxy compound. If desired esterification catalysts or transesterification catalysts can be used, such as sulfuric acid, phosphoric acid, para toluene sulfonic acid, benzene sulfonic acid, stannous octoate, boron trifluoride etherate, tetralkyl titanates and zirconates of U.S. Pat. No. 3,056,818, etc.

Suitable aryl(trihalomethyl) mercury compounds useful in this invention include phenyl (tribromomethyl) mercury, phenyl (dibromochloromethyl) mercury, phenyl (monobromodichloromethyl) mercury, phenyl (trichloromethyl) mercury, phenyl(trifluoromethyl) mercury, etc.

In somewhat greater detail the compounds of this invention can be prepared by reacting a suitable 1,2-dihydrophthalic acid compound with at least one mole of aryl (trihalomethyl) mercury compound in a nonpolar solvent at a temperature of about 20° to 140° C. Usually the 1,2-dihydrophthalic acid compound is dissolved in an inert solvent to form a 1–50% by weight solution preferably 5 to 20% by weight. The aryl (trihalomethyl) mercury compound is then added to the dissolved 1,2-dihydrophthalic acid compound, reacted at about 20° to 140° C and the products are isolated by conventional means.

The mole ratio of aryl (trihalomethyl) mercury compound to 1,2-dihydrophthalic acid compound is dependent upon the particular 1,2-dihydrophthalic acid compound employed. In general, the aryl (trihalomethyl) mercury compound reacts perferentially with free carboxylic acid groups of 1,2-dihydrophthalic acid to form dihalomethyl esters of the 1,2dihydrophthalic acid. Accordingly, in order to produce a bicyclo compound from the free acid, it is necessary to use at least 3 moles of aryl (trihalomethyl) mercury compound per mole of 1,2-dihydrophthalic acid. The main reaction product comprises di-(dihalomethyl) 7,7-dihalobicyclo [4.1.0] hept-4-ene-2,3-dicarboxylate. In those cases where it is desired to produce a tricyclo compound from 1,2-dihydrophthalic acid, it is necessary to react at least 4 moles of aryl (trihalomethyl) mercury compound per mole of 1,2-dihydrophthalic acid. In this case the main reaction product comprises di-(dihalomethyl) 5,5,8,8-tetrahalotricyclo [5.1.0.0$^{4,6}$] octane-2,3-dicarboxylate.

In general, the aryl (trihalomethyl) mercury compounds react preferentially with acyclic olefinically unsaturated double bonds in preference to olefinic double bonds in the 1,2-dihydrophthalate moiety. The acyclic olefinic double bonds are converted to dihalocyclopropane groups. In those cases where a dihydrophthalate diester containing Z equivalents of olefinic unsaturation in the hydroxy moiety is employed, Z + 1 equivalents of aryl (trihalomethyl) mercury compound are required to form a bicyclo compound and Z + 2 equivalents aryl (trihalomethyl) mercury compound per mole of 1,2-dihydrophthalate diester is required to form a tricyclo compound.

Suitable non-polar solvents for carrying out this reaction include hydrocarbon solvents, such as hexane, benzene, toluene, xylenes, etc., halohydrocarbons, such as 1,1,1-trichloroethane, tetrachloroethane, etc.

The resultant bicyclo and tricyclo compound can be added as fire-retardants to resinous polymers, such as polyethylene, polypropylene, polystyrene, polyvinyl chloride, etc. The dimethyl esters can be used in ester-interchange reactions with polyhydric alcohols to produce fire-retardant polyesters or with one of the aforesaid alcohols to produce higher esters, including esters containing olefinic unsaturation in the alcohol portion of the ester or suponified to form the free acid.

The bicyclo compounds, which contain an olefinically unsaturated double bond, can be copolymerized with various addition polymerizable olefinically unsaturated monomers, such as styrene, vinyl toluene, vinyl chloride, vinyl acetate, ethylene, propylene, etc.

EXAMPLE I

Nine and forty-eight hundredths grams phenyl(trichloromethyl) mercury (0.049 moles) were added to a solution of 4.9 grams dimethyl 1,2-dihydrophthalate (0.025 moles) in 125 ml benzene at 80° C contained in a 200 ml flask equipped with stirrer and reflux condenser. After the reactants were refluxed at about 80° C. for five days, the insoluble phenyl mercurous chloride was filtered off and the benzene removed from the filtrate on a rotary evaporator. The insoluble phenyl mercurous chloride was dispersed in 100 ml hexane and filtered yielding 12.43 grams phenyl mercurous chloride (83% of the starting mercury compound). Gas chromatographic analysis showed that dimethyl 1,2-dihydrophthalate had been converted quantitatively into a mixture of 40% by weight dimethyl 7,7-dichlorobicyclo [4.1.0] hept-4-ene-2,3-dicarboxylate (two stereoisomers in a 7:4 ratio) and 60% by weight dimethyl 5,5,8,8-tetrachlorotricyclo [5.1.0.0$^{4,6}$]octane-2,3-dicarboxylate (two isomers in a 3:1 ratio). The bicyclo and tricyclo compounds were separated chromatographically on silica gel (12 grams on 160 grams Davidson 60 silica gel) using hexane. The unreacted phenyl (trichloromethyl) mercury eluted first followed by the tricyclo isomers and then the bicyclo isomers. After the major bicyclo isomer was purified by recrystallization from hexane, it melted at 100°–101° C. Chemical analysis for the bicyclo compound was as follows:

| Calculated for $C_{11}H_{12}O_4Cl_2$ | | Found |
| --- | --- | --- |
| C | 47.34% | 47.20% |
| H | 4.34% | 4.12% |
| Cl | 25.40% | 25.4% |

After the major tricyclo isomer was purified by recrystallization from hexane and sublimation at 80° C/0.4 mmHg, it melted at 136°–136.5° C. Chemical analysis for the tricyclo compound was as follows:

| Calculated for $C_{12}H_{12}O_4Cl_4$ | | Found |
| --- | --- | --- |
| C | 39.81% | 39.61% |
| H | 3.34% | 3.27% |
| Cl | 39.17% | 39.9% |

EXAMPLE II

This example illustrates the preparation of dimethyl 7,7-dibromobicyclo [4.1.0] hept-4-ene-2,3-dicarboxylate and dimethyl 5,5,8,8-tetrabromotricyclo [5.1.0.0$^{4,6}$] octane-2,3-dicarboxylate. Example I was repeated using 5.3 grams dimethyl 1,2-dihydrophthalate (0.27 mole) and 32.0 grams phenyl (tribromomethyl) mercury in 125 ml benzene at 80° C for five days. Seventeen and one-tenth grams phenyl mercurous bromide (80% of the starting mercury compound) was removed by filtration. Column chromatography on silica gel, using hexane and benzene elutants, yielded 63% weight dimethyl 7,7-dibromobicyclo [4.1.0] hept-4-ene-2,3-dicarboxylate (two stereoisomers in a 7:5 ratio) and 37% by weight dimethyl 5,5,8,8-tetrabromotricyclo [5.1.0.0$^{4,6}$] octane-2,3-dicarboxylate (two isomers in a 7:3 ratio). After the major tricyclo isomer was purified by recrystallization from diethyl ether/hexane, it melted at 153°–154° C. Chemical analysis for the tricyclo compound was as follows:

| Calculated for $C_{12}H_{12}Br_4O_4$ | | Found |
| --- | --- | --- |
| C | 26.90% | 26.95% |
| H | 2.26% | 2.39% |
| Br | 59.6% | 59.0% |

We claim:
1. A polyhalocompound selected from at least one member of the group consisting of 7,7-dihalobicyclo [4.1.0] hept-4-ene-2,3-dicarboxylic acid ester and 5,5,8,8-tetrahalotricyclo [5.1.0.0$^{4,6}$] octane-2,3-dicarboxylic acid ester wherein said halo groups are selected from at least one member of the group consisting of fluoro, chloro and bromo and said ester groups are at least one member selected from the group consisting of aliphatic groups containing from 1 to 24 carbon atoms, aromatic groups containing from 6 to 24 carbon atoms and aralkyl groups containing from 7 to 25 carbon atoms.

2. The compound of claim 1, wherein said polyhalo compound comprises a dialkyl ester containing from 1 to 24 carbon atoms.

3. The compound of claim 1, wherein said polyhalo compound comprises dimethyl 7,7-dibromobicyclo [4.1.0] hept-4-ene-2,3-dicarboxylate.

4. The compound of claim 1, wherein said polyhalo compound comprises dimethyl 7,7-dichlorobicyclo [4.1.0] hept-4-ene-2,3-dicarboxylate.

5. The compound of claim 1, wherein said polyhalo compound comprises dimethyl 5,5,8,8-tetrabromo-tricyclo 8 5.1.0.0$^{4,6}$] octane-2,3-dicarboxylate.

6. The compound of claim 1, wherein said polyhalo compound comprises dimethyl 5,5,8,8-tetrachloro-tricyclo [5.1.0.0$^{4,6}$] octane-2,3-dicarboxylate.

* * * * *